United States Patent
Peyman

(10) Patent No.: US 7,101,571 B2
(45) Date of Patent: Sep. 5, 2006

(54) METHOD AND COMPOSITION FOR HYPERTHERMALLY TREATING CELLS

(76) Inventor: Gholam A. Peyman, 8654 Pontchartrain Blvd., Unit #1, New Orleans, LA (US) 70124

( * ) Notice: Subject to any disclaimer, the term of this patent is extended or adjusted under 35 U.S.C. 154(b) by 119 days.

(21) Appl. No.: 10/073,863

(22) Filed: Feb. 14, 2002

(65) Prior Publication Data

US 2003/0152517 A1    Aug. 14, 2003

(51) Int. Cl.
*A61K 9/127* (2006.01)
(52) U.S. Cl. .................................... 424/450
(58) Field of Classification Search ................ 424/450
See application file for complete search history.

(56) References Cited

U.S. PATENT DOCUMENTS 3,993,754 A * 11/1976 Rahman et al.
4,891,043 A   1/1990 Zeimer et al.
5,094,854 A   3/1992 Ogawa et al.
5,149,319 A   9/1992 Unger
5,935,942 A * 8/1999 Zeimer
5,976,502 A * 11/1999 Khoobehi et al.
6,248,727 B1  6/2001 Zeimer

* cited by examiner

*Primary Examiner*—Humera N. Sheikh
(74) *Attorney, Agent, or Firm*—Roylance, Abrams, Berdo & Goodman, L.L.P.

(57) ABSTRACT

A method for the hyperthermia treatment of tissue in a target site applies a heat source to kill cells without protein denaturization. The method introduces an encapsulated dye that is released at a selected temperature in the target site to indicate that a threshold temperature has been reached to hyperthermally treat the tissue. In one embodiment, the composition releases the dye at a temperature of 42° C. to 50° C., and preferably about 45° C. to 49° C. The composition which can be a liposome composition encapsulating the dye can be introduced to the bloodstream of the patient to flow through the target site.

35 Claims, 1 Drawing Sheet

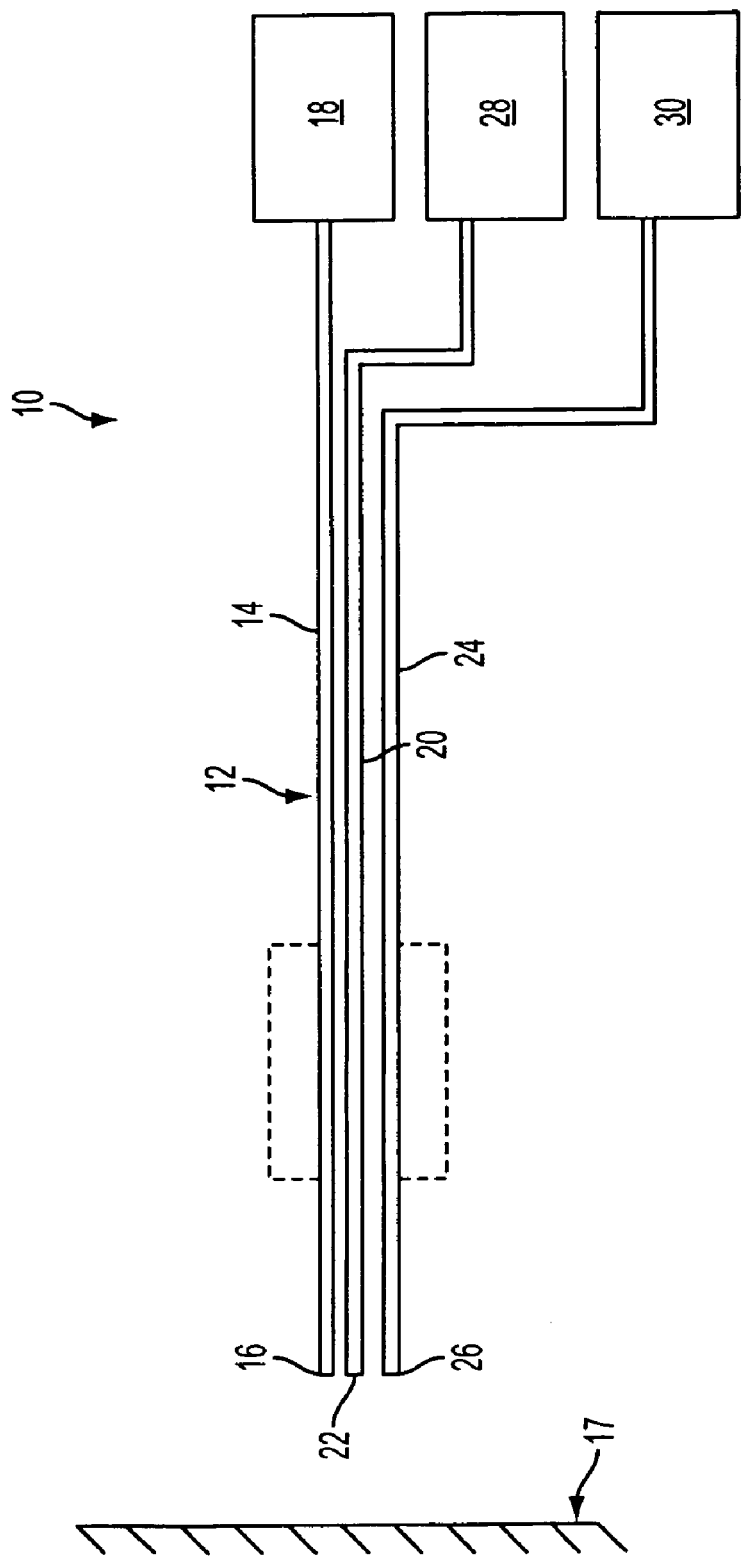
FIGURE

METHOD AND COMPOSITION FOR HYPERTHERMALLY TREATING CELLS

FIELD OF THE INVENTION

The present invention relates to a method and composition for hyperthermally treating cells at a site in the body. More particularly, the present invention relates to a method for treating cells at a target site in the body, such as at a lens capsule of an eye, tumors, and exudative ARM (age related macular degeneration) by applying thermal energy to the target site to heat the cells to a temperature which will kill the cells or impede cell multiplication without exceeding the protein denaturation temperature of the tissue.

BACKGROUND OF THE INVENTION

Several techniques currently exist for treating cells at a selected site in the body with heat or chemicals to kill or impede multiplication of those cells to prevent undesired cell proliferation. For example, numerous types of chemotherapy drugs exists which, when injected into a tumor or delivered systemically to a patient, attack and kill cancerous cells to prevent them from further multiplying.

Radiation techniques can also be used to kill cancerous or other undesired cells. Cell death begins to occur when the cells are heated to a temperature of about 5° C. or more above the normal body temperature of 37° C. Applying radiation to a localized site in the body, such as a tumor or other area containing undesired cells, can heat the cells at the site to temperatures in excess of 60° C. Such high temperatures causes a phenomenon known as protein denaturation to occur in the cells, which results in immediate cell death. Accordingly, radiation therapy has been suitable in successfully treating certain types of cancers and other diseases involving uncontrolled cell growth.

Other types of heating techniques, such as the use of probes or catheters to provide localized heat to a site of interest also exist. Like radiation therapy, these techniques also heat the cells to a temperature sufficient to cause protein denaturation in the cells to thus kill the cells quickly.

Photosensitive chemicals are also used to kill cells at certain sites of interest in the body. For example, a photosensitive chemical can be injected directly into a site of interest to expose cells at that site to the chemical. A light emitting source, which emits light at a wavelength that will activate the photosensitive chemical, is then focused on the site of interest. Accordingly, the light activates the photosensitive chemical that has been absorbed by or is otherwise present in the cells of interest. The activated chemical kills the cells, which thus prevents undesired cell proliferation.

Although the techniques mentioned above can be suitable for preventing certain types of cell proliferation and certain sites in the body, several drawbacks with these techniques exist. For example, often the use of chemotherapy drugs alone to treat a tumor or cancerous site is insufficient to kill the undesired cells. Moreover, the chemotherapy drugs also kill many normal healthy cells along with the cancerous cells, which can adversely affect the patient's health.

The use of radiation in conjunction with chemotherapy can have a more detrimental effect on the cancerous cells. However, as with chemotherapy, radiation often kills normal healthy cells, such as those in front of or behind the site of interest, along with the cancerous cells. Moreover, the intense heating of the cells can cause the cells to coagulate and thus block the capillaries at the site of interest. The blocked capillaries therefore prevent chemotherapy drugs from reaching the site of interest.

One example of a method of chemically treating a target site is disclosed in U.S. Pat. No. 6,248,727 to Zeimer. This method delivers a liposome containing a fluorescent dye and tissue-reactive agent. The liposome is administered intravenously to flow to the locus in the eye of the patient and the site is non-invasively heated to release the dye and the tissue-reactive agent. The dye is fluoresced to observe the pattern of the fluorescence. The tissue-reactive agent is activated to chemically damage and occlude the blood vessel. The liposomes are selected to release the dye at a temperature of 41° C. or less without causing thermal damage to the blood vessel.

In addition, the above techniques have not been used to prevent unwanted cell proliferation at certain locations in the eye, such as at the retina or at the lens capsule. Because the retina is very sensitive, conventional radiation techniques can be too severe to treat cancerous cells on, in or under the retina.

Also, after cataract surgery, a phenomenon known as capsular opacification and, in particular, posterior capsular opacification can occur in which the epithelial cells on the lens capsule of the eye experience proliferated growth. This growth can result in the cells covering all or a substantial portion of the front and rear surfaces of the lens capsule, which can cause the lens capsule to become cloudy and thus adversely affect the patient's vision. These cells can be removed by known techniques, such as by scraping away the epithelial cells. However, it is often difficult to remove all of the unwanted cells. Hence, after time, the unwanted cells typically will grow back, thus requiring further surgery.

Accordingly, a need exists for a method for hyperthermally treating tissue and preventing unwanted cell proliferation at sites in the body, especially at sites in the eye such as the retina, choroid and lens capsule, which does not suffer from the drawbacks associated with the known techniques discussed above.

SUMMARY OF THE INVENTION

The present invention is directed to a method of hyperthermally treating tissue by heating the tissue above a temperature which kills cells in the tissue. In particular, the invention is directed to a method of heating tissue above a temperature effective to treat the tissue without denaturing the protein.

Accordingly, a primary aspect of the invention is to provide a method for heating tissue at least to a temperature sufficient to hyperthermally treat the tissue.

Another aspect of the invention is to provide a method of hyperthermally treating tissue to a temperature sufficient to kill cells in the tissue and at a temperature below the protein denaturization temperature of the tissue.

A further aspect of the invention is to provide a method of hyperthermally treating tissue, where the tissue includes or is provided with a temperature indicator to indicate a hyperthermally effective temperature of the tissue.

Still another aspect of the invention is to provide a method of hyperthermally treating tissue where a temperature indicator composition is introduced into the tissue or bloodstream near the tissue to indicate a tissue temperature effective to hyperthermally treat the tissue and a temperature indicator to indicate a tissue temperature above a protein denaturization temperature of said tissue.

A further aspect of the invention is to provide a method of hyperthermally treating tissue by introducing a temperature indicator into the tissue and heating the tissue to a temperature where the temperature indicator can be detected. In a preferred embodiment, the temperature at which the indicator can be detected is a temperature effective to hyperthermally treat the tissue and is at a temperature below the protein denaturization temperature.

A further aspect of the invention is to provide a method of heating and detecting a temperature of a tissue between a first temperature and a second temperature. The method introduces a temperature indicator into the tissue. The temperature indicator includes a first dye that can be detected at the first temperature to indicate that the first temperature has been reached, and a second dye that can be detected at the second temperature to indicate that the second temperature has been reached.

Still another aspect of the invention is to provide a temperature indicating composition for introducing into a tissue to be thermally treated. The composition includes a first dye encapsulated in a heat sensitive liposome where the first dye is releasable at a temperature effective to hyperthermally treat the tissue and at a temperature below the protein denaturization temperature. The composition also includes a second dye encapsulated in a second liposome where the second dye is releasable at a temperature at or above the protein denaturization temperature.

Another aspect of the invention is to provide a method to hyperthermally treat tissue to kill the tissue cells substantially without protein denaturization of the tissue where the tissue includes a heat sensitive liposome containing a temperature indicating dye and a temperature activated bioactive compound. The tissue is heated to release the dye from the liposome to indicate a thermally effective temperature to kill cells in the tissue at a temperature below the protein denaturization temperature. The heat applied to the tissue simultaneously releases the bioactive compound to treat the tissue.

The various aspects of the invention are basically attained by providing a method of hyperthermally treating tissue in an animal. The method comprises the step of introducing a temperature indicating substance into the bloodstream of the animal to flow through a target site. The temperature indicating substance includes a fluorescent dye encapsulated within a heat sensitive liposome. The fluorescent dye is releasable from the liposome at a temperature of at least 41° C. A heat source is applied to the target site and the target is hyperthermally heated to at least 41° C. to release and fluoresce the dye and to hyperthermally treat the target site for a time sufficient to kill cells in the tissue.

The aspects of the invention are also attained by providing a method of detecting a threshold temperature and of hyperthermally treating tissue in an animal. The method comprises the step of introducing a first fluorescent dye encapsulated in a first heat sensitive liposome into the bloodstream of an animal in a location to flow through a target site in the animal. The first fluorescent dye is releasable from the first heat sensitive liposome at a temperature of at least 41° C. The target site is heated to a temperature to release the first fluorescent dye and the first fluorescent dye is fluoresced to indicate and visualize a tissue temperature of at least 41° C. Heating of the target site is continued at a temperature of at least 41° C for a time sufficient to hyperthermally treat the tissue.

The aspects of the invention are further attained by providing a method of hyperthermally treating tissue of an animal. The method comprises the step of introducing a temperature indicating substance into the bloodstream of the animal to flow through a target site. The temperature indicating substance includes a first fluorescent dye encapsulated in a first temperature sensitive liposome. The first fluorescent dye is releasable from the first liposome by heating to a temperature of at least 42° C. A second fluorescent dye encapsulated in a second temperature sensitive liposome is also included. The second fluorescent dye is releasable from the second liposome by heating to a temperature of at least 50° C. The target site is heated to a temperature of at least 42° C. The first fluorescent dye is fluoresced to indicate an effective temperature for hyperthermally treating the tissue without releasing the second fluorescent dye from the second liposomes.

These and other aspects of the invention will become apparent to one skilled in the art in view of the following detailed description of the invention.

BRIEF DESCRIPTION OF THE DRAWINGS

The following is a brief description of the drawing, in which:

The FIGURE is a schematic diagram of one embodiment of the invention showing a probe for hyperthermally treating tissue and visualizing a dye in the target site.

DETAILED DESCRIPTION OF THE INVENTION

The present invention is directed to a method and composition for hyperthermally treating tissue. In particular, the invention is directed to as method for heating tissue above a temperature effective to kill tissue cells or inhibit multiplication of cells below the protein denaturization temperature of the tissue.

The method of the invention introduces a composition into the bloodstream of the body in a location to flow into or through a target site to be treated. A heat source is applied to the target site to heat the tissue in the target site for a time sufficient to hyperthermally treat the tissue and activate the composition. As used herein, the term "hyperthermal" refers to a temperature of the cell or tissue that kills or damages the cells without protein denaturization.

The composition contains a temperature indicator that is able to provide a visual indication when a minimum or threshold temperature is attained that is sufficient to hyperthermally treat the tissue. It is a feature of the invention to provide a method of heating tissue in a target site to a hyperthermally effective temperature and to provide a visual indication that a temperature of at least 41° C., and preferably at least 42° C. is attained. In one embodiment, the composition includes a second temperature indicator to provide a visual indication when a protein denaturization temperature is attained thereby providing an indication that a maximum desired temperature is exceeded. The heat source can be applied to the tissue so that the composition provides an indication that a thermally effective temperature is attained that is below the protein denaturization temperature of the tissue.

In one embodiment of the invention, the method introduces a composition to a target site, where the composition includes a fluorescent dye that is encapsulated in a heat sensitive particle, such as a liposome. The dye is a fluorescent dye that can be excited to fluoresce and be observed or visualized by the operator. Preferably, the heat sensitive liposomes are formed to rupture or release the fluorescent dye at a temperature at least equal to the temperature necessary to kill cells in the tissue and at a temperature below the protein denaturization temperature. The composition containing the heat sensitive liposomes encapsulating the fluorescent dye is introduced into the bloodstream to flow to or through the target site. The amount of the liposome composition is introduced in an amount effective to be released in or near the target site and to excited and visualized by the exciting light source and the visualizing device. The composition containing the dye can be injected in a single dose into the bloodstream or injected continuously to supply a continuous flow of the composition through the target site. The amount of the composition introduced can vary depending on the target site and the length of time that the dye is to be excited. A light or energy source is continuously applied to the target site to excite the dye and to cause the dye to fluoresce when released from the liposomes. An imaging device is used to capture the fluorescing light from the dye to provide a visual indication that the dye is released. The release temperature of the liposomes are selected to release the dye at a predetermined temperature so that when the dye is fluoresced and visualized, the visualization provides the operator with an indication that the release temperature in the target site has been attained. In one embodiment, the liposome composition is injected into the blood stream so that the composition is able to provide a continuous supply of the dye for fluorescing during the hyperthermal treatment. In this manner the operator is provided with a continuous indication that a sufficient temperature is being maintained.

The method of the invention is primarily directed to a method of heating tissue and cells in the tissue of an animal, particularly a human patient, at least to the temperature sufficient to kill or damage the cells. Cell death or cell damage is known to occur when the tissue cells are heated to a temperature of about 5° C. above the normal body temperature of 37° C. Therefore, the method of the invention heats the cells in the tissue to a temperature of about 41° C., and preferably at least 42° C. for a time sufficient to kill or damage the cells. Preferably, the heat source is applied to minimize unnecessary damage to the surrounding cells and tissue.

In one embodiment of the invention, the tissue is heated to a temperature of at least 41° C. and preferably in the range of at least about 42° C. to about 50° C. Heating the tissue to at least 42° C. ensures that a sufficient temperature is obtained to thermally treat the tissue and the cells effectively. Preferably, the tissue is heated to a temperature below the protein denaturization temperature of the tissue. Protein denaturization begins to occur at about 50° C. to 51° C. and occurs rapidly at temperatures of about 60° C. Preferably, the tissue is heated to a temperature of less than 60° C. and more preferably to a temperature of about 50° C. or less.

In one preferred embodiment, the tissue and the cells are heated to a temperature of about 47° C. to about 49° C. for a time sufficient to kill or damage the cells without protein denaturization. The length of time that the tissue is heated will depend on the location of the target site, the size and dimensions of the target site, the desired depth of penetration of the heat and the desired extent of thermal treatment or damage of the tissue and cells in the target site. Typically, the heat source is applied for several minutes. In one embodiment, the heat source is applied for about 1 to 15 minutes, and typically about 5 to 10 minutes.

The heat source can be applied to a variety of the areas in the body where the hyperthermal treatment is desired. The target site can be tumors, organs, muscles and soft tissue. Examples of a target site include blood vessels and arteries, esophagus and eyes. In one embodiment, the method is suitable for hyperthermally treating the epithelial cells on the lens of the eye after cataract surgery. Other target sites include the retina and the choroid.

The target site is heated to the desired temperature to hyperthermally treat the target site using standard heating instruments and equipment for heating tissue and standard equipment for visualizing the dye in the target site that has been released from the heat sensitive particles. For example, the heating equipment preferably includes suitable heat or energy source that is able to focus the heat or energy on the target and is able to control heat and temperature of the tissue. The heat source can be an electrical resistance heating element, or an indirectly heated element. The heating device can also have an energy source for producing heat at the target site, such as a radio frequency (RF) device, ultrasonic generators, laser, or infrared device. One example of an RF generator device for hyperthermally treating tissue in a selected target site is disclosed in U.S. Pat. No. 6,197,022, which is hereby incorporated by reference in its entirety. Examples of suitable ultrasonic devices for delivering ultrasonic hyperthermia are disclosed in U.S. Pat. Nos. 4,620,546, 4,658,828 and 4,586,512, the disclosures of which are hereby incorporated by reference in their entirety.

In one embodiment, the heat source includes a probe having a tip with the heating element or energy emitting element attached thereto. The energy emitting element can be an optical fiber operatively connected to a laser, infrared or ultraviolet light source. The probe preferably includes a suitable control mechanism for manipulating the probe to the target site and a control for controlling the energy applied to the target site.

A suitable device for hyperthermally treating the tissue in a target site is shown in the FIGURE. The device 10 includes a probe 12 having an optical fiber 14 with a distal end 16 for emitting a laser light to heat the tissue 17. Preferably, the end 16 of optical fiber 14 can focus the light source on the target site 17. Optical fiber 14 is connected to laser generator 18 that is able to generate a laser beam of sufficient intensity and within wavelength for hyperthermally treating tissue to a temperature of at least 41° C. and preferably at least 42° C.

In a preferred embodiment, probe 12 includes a second optical fiber 20 having a distal end 22 and a third optical fiber 24 having a distal end 26. Optical fiber 20 is operatively connected to a light source 28, such as a laser, that is able to emit a light beam having a wavelength capable of fluorescing a fluorescent dye in the target area when the dye is released from the heat sensitive particles. Optical fiber 24 is operatively connected to a suitable imaging device 30 for capturing the fluoresced light from the excited dye and visualizing and producing an image of the fluorescing dye in the target site. Imaging device 30 can be a CCD or a device equivalent to a funduscope. An example of a suitable funduscope is disclosed in U.S. Pat. No. 4,891,043 to Zeimer, which is hereby incorporated by reference in its entirety.

In another embodiment of the invention, the probe can include a heating element or a device for receiving a heated fluid that can transfer the heat to the tissue in the target site. The probe can include an expandable bladder member for receiving a heated fluid delivered from a fluid-heating source. In still another embodiment, the expandable bladder includes a permeable portion so that the heated fluid can be applied directly to the target site. A suitable aspirating device is preferably included to remove the excess heating fluid when applied directly to the target site.

In one embodiment, the target site is the retina or choroid in the eye of the patient. The heating and visualizing instrument includes a laser capable of focusing a laser beam on the target site where the laser beam has a wavelength and intensity to heat the cells to a temperature of at least 42° C. In one embodiment, the laser heats the cells to a temperature of 50° C. or below and preferably to about 42° C. to 50° C. The instrument also includes or is used in combination with a funduscope to excite or fluoresce the dye that has been released in the target site to capture and visualize the fluorescing dye. A funduscope that can be used is disclosed in U.S. Pat. No. 6,248,727, which is hereby incorporated by reference in its entirety. The laser source is selected to provide sufficient energy to heat the tissue in the target site to the desired temperature.

The fluorescent dye is encapsulated in a suitable heat sensitive particle and introduced into the patient in a location to be visualized in the target site. The heat sensitive particles can be microcapsules, or nanocapsules that are able to release the dye at a temperature of about 41° C., and preferably 42° C. or higher. In preferred embodiments, the fluorescent dyes are incorporated into heat sensitive liposomes that have a phase transition temperature at the temperature of hyperthermia. In one embodiment, the liposomes have a phase transition temperature within the desired temperature range that tissue or cells are to be heated.

In one embodiment, the liposomes have a phase transition temperature of at least 41° C. and preferably at least 42° C. In a preferred embodiment, the liposomes have a phase transition temperature of about 45° C. to about 50° C.

The liposomes can be made by various processes as known in the art. The phase transition temperature of the phospholipid is selected to control the temperature that the dye and other components are released from the liposomes. Phospholipids are known to have different phase transition temperatures and can be used to produce liposomes having release temperatures corresponding to the phase transiture of the phospholipids. Suitable phospholipids include, for example, dimyristoylphosphatidyl choline having a phase transition temperature of 23.9° C., palmitoylmyristoylphosphatidyl choline having a phase transition temperature of 27.2° C., myristolypalmitoylphosphatidyl choline having a phase transition temperature of 35.3° C., dipalmitoylphosphatidyl choline having a phase transition temperature of 41.4° C. stearoylpalmitoylphosphatidyl choline having a phase transition temperature of 44.0° C., palmitoylstearolyphosphatidyl choline having a phase transition of 47.4° C., and distearolyphosphatidyl choline having a phase transition temperature of 54.9° C. Another suitable phospholipid is a synthetic $C_{17}$ phosphatidyl choline from Aventi Inc. having a phase transition temperature of about 48° C.–49° C.

The phase transition temperature and the release temperature of the liposomes can be selected by combining the different phospholipids during the production of the liposomes according to the respective phase transition temperature. The phase transition of the resulting liposome membrane is generally proportional to the ratio by weight of the individual phospholipids. Thus, the composition of the phospholipids are selected based on the respective phase transition temperature so that the phase transition temperature of the liposome membrane will fall within the selected range. By adjusting the phase transition temperature of the liposome membrane to the selected range, the temperature at which the liposomes release the dyes and other components can be controlled during hyperthermia.

The liposomes in one embodiment of the invention are preferably prepared so that the liposome membrane has a phase transition temperature of at least 42° C., and preferably about 42° C. to about 50° C. In a preferred embodiment, the liposomes leak or rupture at a temperature of about 49° C. or less, and typically between about 45° C. and 49° C. In one embodiment, the phospholipids have saturated acyl groups. For example, glycerophospholipids can be used that have two acyl groups having 8 or more carbon atoms and where at least one of the acyl groups have at least 10 carbon atoms and typically 12–18 carbon atoms. Examples of suitable phospholipids include hydrogenated lecithin from plants and animals, such as egg yolk lecithin and soybean lecithin. The phospholipid can also be phosphatidyl choline produced from partial or complete synthesis containing mixed acyl groups of lauryl, myristoyl, palmitoyl and stearoyl.

The liposomes can be prepared from a mixture of dipalmitoylphosphatidyl choline and disteroylphosphatidyl choline in a weight ratio of 95:5 to about 5:95 and generally about 80:20 to about 20:80. In one embodiment, the liposomes are made from a mixture of dipalmitoylphosphatidyl choline and disteroylphosphatidyl choline in a ratio of 45:55 to about 55:45 provide a phase transition temperature of about 46° C. to about 49° C.

The liposomes of the invention can be prepared by standard processes as known in the art. The liposomes can be unilamellar or multilamellar and have a particle suitable for delivering the dye to the target site. In one embodiment, the liposomes have a particle size of a sufficiently small size to be introduced into the bloodstream of the patient in a location near the target site to flow through the target site.

The liposomes can contain a suitable osmotic pressure controlling agent that is physiologically acceptable to the patient. Examples include sodium chloride, sugars such as glucose, mannitol and sorbitol, and amino acids such as glycine, aspartic acid and glutamic acid. Examples of suitable process for preparing liposomes are disclosed in U.S. Pat. No. 4,235,871 to Papahadjopoulos et al. and U.S. Pat. No. 4,522,803 to Lenk, which are hereby incorporated by reference in their entirety.

The liposomes of the invention contain a dye that is able to fluoresce and that can be visualized in the target site by exciting with a light source that is amenable to the target site and the patient. The fluorescent dye can be any fluorescent that is suitable for encapsulation and is physiologically compatible. Preferably, the fluorescent dye is quenched when encapsulated at an appropriate concentration. The quenching concentration is a sufficiently high concentration to mask or minimize detection of fluorescence when illuminated by a fluorescing light source. The quenching concentration can be determined by routine experimentation as known in the art. When heated, the heat sensitive liposomes rupture or leak the dye and other components of the liposome so that the dye is diluted in the target site to a suitable concentration where the dye can be fluoresced and visualized upon excitation by a suitable light source. Examples of suitable dyes include 6-carboxyfluorescein and its derivatives. Suitable fluorescent dyes can be excited by an emit light at wavelengths that are not strongly absorbed by the tissue. Other suitable dyes include indocyanin green and aluminum phthalocyanine tetrasulfonate. It will be understood that the fluorescing light source and the visualizing instrument are selected according to the wavelength of the fluorescing dye to visualize the dye.

In one embodiment, the dye is selected to fluoresce in the presence of a light from an argon laser, a helium-neon laser or infrared laser. Preferably the dye is selected to be compatible with the exciting light or laser source to fluoresce when subjected to the light or laser beam. A suitable dye is sold under the tradename D-275 by Molecular Probe, Inc. and fluoresces green when exposed to light from an argon laser at 484 nm. A dye sold under the tradename D-1121 fluoresces orange when exposed to a long wavelength laser light at 560–574 nm. On preferred dye is an infrared excitable dye $DiIc_{18}(7)$, which fluoresces at a wavelength of 740–780 nm.

In one embodiment of the invention, a fluorescent dye is encapsulated in liposomes having a phase transition temperature of 42° C. to 50° C., and preferably about 45° C. to 49° C. In another embodiment, the liposomes have a phase transition temperature to release the dye at a temperature of about 46° C. to about 49° C. The liposomes are injected into the bloodstream of the patient in a location where the liposomes flow to the target site. In some embodiments, the liposomes can be introduced directly to the target site intravenously, subcutaneously or topically. A hyperthermal heat source and a dye exciting light source are applied to the target site. The hyperthermal heat source, which is preferably a laser light beam, is focused on the target site to heat the tissue and the cells to a temperature of at least 42° C. to hyperthermally treat the tissue and kill the cells. The hyperthermal heat source also heats the liposomes to a temperature at least equal to the phase transition temperature to release the dye. The fluorescing light source excites the dye so that the fluorescing dye in the target site can be detected and visualized. By encapsulating the fluorescent dye in liposomes having a phase transition of at least 42° C., the detection of the fluorescing dye provides a positive indication to the operator that the desired tissue temperature has been obtained that is necessary to hyperthermally treat the tissue. The phase transition temperature of the liposomes is selected according to desired minimum temperature that the tissue is to be heated. The hyperthermia energy source is applied to the target site for a time sufficient to treat the tissue to the desired level. Generally, the tissue is heated to a temperature of at least 42° C. for 1–15 minutes and preferably 1–10 minutes.

In one preferred embodiment of the invention, the liposomes contain a suitable drug or photosensitizing agent. The drugs preferably show a synergistic effect when combined with the hyperthermia treatment of the invention. The release of the drugs from the liposomes provide an improved targeting effect by releasing the drugs by the heat source in the target site. Suitable drugs include antitumor agents such as cisplatin, carboplatin, tetraplatin and iproplatin. Suitable anticancer drugs include adriamycin, mitomycin C, actinomycin, ansamitocin and its derivatives, bleomycin, Ara-C, daunomycin, metabolic antagonists such as 5-FU, methotrexate, isobutyl 5-fluoro-6-E-furfurylideneamino-xy-1,2,3,4, 5,6 hexahydro-2,4-dioxopyrimidine-5-carboxylate. Other antitumor agents include melpharan, mitoxantrone and lymphokines. The amount of the particular drug entrapped in the liposomes are selected according to the desired therapeutic dose and the unit dose.

Examples of suitable photosensitive (photosensitizer) agents include aminolevolunic acid, porphyrine derivatives, porpurine derivatives, NPE-6, ATX-10, plant derived photosensitizers. Other synthetic sensitizers such as $SNET_2$ and Lutex can be used. Preferably, the photosensitizers are used in non-toxic amounts. In other embodiments, the liposome compositions can contain liposomes that encapsulate a hyperthermic potentiating agent such as perfluorooctyliodide, perfluorotributylamine, perfluorotripropylamine, and perfluorooctylbromide. Examples of liposome encapsulated potentiators are disclosed in U.S. Pat. No. 5,149,319 to Unger, which is hereby incorporated by reference in its entirety. Other bioactive agents that can be delivered to the target site by encapsulating in liposomes include anti-inflammatory agents, antibiotics, antibacterial agents, antifungal agents, anti-neoplastic agents and antiparasitic agents. Examples of anti-neoplastic agents include aclacinomycins, chromycins and olivomycins.

In another embodiment of the invention, the liposome composition contains a mixture of liposomes having different phase transition temperature to release the components at different temperatures. In one embodiment, the liposome composition contains liposomes encapsulating a first dye and having a phase transition temperature of 42° C. to about 45° C. and liposomes encapsulating a second dye and having a phase transition temperature of about 50° C. or higher. In one embodiment, the second dye is encapsulated in liposome that release the dye at a temperature range of 50° C. to 60° C. Preferably, the second dye is able to fluoresce at different color than the first dye so that the dyes are distinguishable. In this embodiment, the liposome composition is delivered to the target and the target site is subjected to hyperthermia temperatures. As the tissue in the target site is heated to at least 42° C., the first liposomes rupture or release the first dye so that the first dye is visualized and detected in the target site. The detection of the first dye in the target site enables the operator to monitor the temperature of the tissue in the target site and to indicate that a hyperthermal temperature has been attained in the tissue at the target site. During hyperthermia, it is difficult to determine and monitor the actual temperature of the tissue and care must be taken to avoid overheating of the tissue and denaturization of the proteins. In preferred embodiments of the invention, the hyperthermal treatment does not exceed the protein denaturization temperature. In this embodiment, the second liposomes are selected to rupture or release the second dye at or slightly below the protein denaturization temperature. In this manner, the second dye is released and visualized to provide the operator with an indication that the tissue is heated to the protein denaturization temperature. The heat source is then adjusted by the operator to reduce the energy applied to the target site to avoid protein denaturization.

In another embodiment, the liposome composition can contain several liposomes that can leak or rupture at different temperatures to release the dyes at incremental temperatures as the temperature of the target site increases. In one embodiment, the liposomes can be selected to leak or rupture the dye at 2° C. intervals between about 42° C. and 50° C. The dyes for each liposome can be different to fluoresce a different color so that the different colors indicate a different temperature of the target site.

In other embodiments of the invention, the tissue in the target site can be irradiated by beta radiation from strontium or iridium isotopes. Gamma radiation from $P^{32}$, iodine-95, and palladium-90 can also be used. The radioactive isotopes can be delivered as small particles to the target site in combination with the hyperthermia treatment.

Although several embodiments have been chosen to illustrate the invention, those skilled in the art will readily appreciate that various changes and modifications can be made without departing from the scope of the invention.

What is claimed is:

1. A method of hyperthermally treating tissue in an animal, said method comprising the steps of:

introducing a temperature indicating substance into the bloodstream of said animal to flow through said tissue in a target site, said temperature indicating substance comprising a fluorescent dye encapsulated within a heat sensitive liposome, said fluorescent dye being releasable from said liposome at a temperature of about 45° C. to about 49° C., and introducing a second dye encapsulated in a second liposome where the second dye is releasable at a temperature at or above the protein denaturization temperature applying a heat source to said target site and hyperthermally heating said tissue in said target site to at least 47° C. to release said dye and to hyperthermally treat said tissue in said target site for a time sufficient to kill cells in said tissue substantially without denaturing proteins in said tissue, and fluorescing and visualizing said dye to indicate that a predetermined temperature has been attained at said target site.

2. The method of claim 1, wherein said liposome encapsulates a bioactive compound, and said method comprises heating said liposome to release said bioactive compound.

3. The method of claim 2, wherein said bioactive compound is heat activated.

4. The method of claim 2, wherein said bioactive compound is an antiproliferative agent or an antitumor agent.

5. The method of claim 2, wherein said bioactive compound is selected from the group consisting of cisplatin, carboplatin, tetraplatin, iproplatin, adriamycin, mitomycin C, actinomycin, ansamitocin and bleomycin.

6. The method of claim 1, wherein said heat source is a laser source, a microwave source, an infrared source, or an ultrasonic source.

7. The method of claim 1, wherein said heat source is a heated fluid source, and where said method comprises applying said heated fluid to said target site.

8. A method of detecting a threshold temperature and hyperthermally treating tissue in an animal, said method comprising the steps of:
introducing a first fluorescent dye encapsulated in a first heat sensitive liposome into the bloodstream of an animal in a location to flow through a target site in said animal, said first fluorescent dye being releasable from said first heat sensitive liposome at a temperature of about 45° C. to 49° C., introducing a second dye encapsulated in a second liposome where the second dye is releasable at a temperature at or above the protein denaturization temperature and
heating said target site to a temperature to release said first fluorescent dye and fluorescing said first fluorescent dye to indicate and visualize a tissue temperature when said tissue reaches a temperature of at least 45° C., and continuing heating said target site for a time sufficient to hyperthermally treat said tissue and kill cells in said tissue and at a temperature below a protein denaturing temperature.

9. The method of claim 8, comprising heating said target site to a temperature between about 47° C. and about 49° C. for about 1–10 minutes.

10. The method of claim 8, wherein said first liposome encapsulates a bioactive compound, and wherein said method comprises heating said first liposome to release said bioactive compound.

11. The method of claim 10, wherein said bioactive compound is heat activated.

12. The method of claim 10, wherein said bioactive compound is an antiproliferative agent or an antitumor agent.

13. The method of claim 10, wherein said bioactive agent is selected from the group consisting of cisplatin, carboplatin, tetraplatin, iproplatin, adriamycin, mitomycin C, actinomycin, ansamitocin and bleomycin.

14. The method of claim 8, wherein said heat source is a laser source, a microwave source, an infrared source or an ultrasonic source.

15. The method of claim 8, wherein said heat source is a source of heated fluid and said method comprises applying said heated fluid to said target site.

16. The method of claim 8, wherein said second fluorescent dye being releasable from said second liposome at a temperature of at least 50° C., and
visualizing and detecting said second fluorescent dye released from said second liposomes and reducing said temperature of said tissue to a temperature below 50° C. in response to said detected second dye.

17. The method of claim 16, wherein said second fluorescent dye is released from said second liposome at a temperature where protein denaturization occurs, and wherein said temperature of said tissue is reduced below the protein denaturization temperature in response to said detected second fluorescent dye.

18. The method of claim 16, comprising heating said tissue in said target site to a temperature below a protein denaturization temperature of said tissue and below said release temperature of said second fluorescent dye.

19. A method of hyperthermally treating tissue of an animal, said method comprising the steps of:
introducing a temperature indicating substance into the bloodstream of said animal to flow through a target site, said temperature indicating substance comprising a first fluorescent dye encapsulated in a first temperature sensitive liposome, said first fluorescent dye being releasable from said first liposome by heating to a temperature of about 45° C. to about 49° C., and introducing a second fluorescent dye encapsulated in a second temperature sensitive liposome, said second fluorescent dye being releasable from said second liposome by heating to a temperature of at least 50° C., and
heating said target site and said first temperature sensitive liposome to a temperature sufficient to release said first liposome, and fluorescing said first fluorescent dye to indicate an effective temperature of at least 45° C. for hyperthermally treating said tissue without releasing said second fluorescent dye from said second liposomes.

20. The method of claim 19, comprising monitoring and detecting a fluorescence of said second fluorescent dye when released from said second temperature sensitive liposome and reducing said temperature of said tissue below a protein denaturing temperature of said tissue in response to a detection of said second fluorescent dye released from said second temperature sensitive liposome.

21. The method of claim 19, wherein said first fluorescent dye fluoresces a color different from a color of said second fluorescent dye.

22. The method of claim 19, wherein said first liposome comprises a phospholipid selected from the group consisting of dipalmitoylphosphatidyl-choline, dipalmitoylpyhosphatidyl-glycerol, and mixtures thereof.

23. The method of claim 19, wherein said first liposome comprises a $C_{17}$-phosphatidyl-choline, wherein said second liposome releases said second fluorescent dye at a temperature of about 48° C. to 49° C.

24. A method of hyperthermally treating tissue of an animal, said method comprising the steps of:
introducing a temperature indicating substance into the bloodstream of said animal to flow through a target site, said temperature indicating substance comprising a first fluorescent dye encapsulated in a first temperature sensitive liposome, said first fluorescent dye being releasable from said first liposome by heating to a temperature of about 45° C. to about 49° C., and introducing a second fluorescent encapsulated in a second temperature sensitive liposome, said second fluorescent dye being releasable from said second liposome by heating to a temperature of at least 50 C, wherein said first liposomes encapsulate a bioactive compound, and heating said target site and said first temperature sensitive liposome to a temperature sufficient to release said first liposome, and fluorescing said first fluorescent dye to indicate an effective temperature of at least 45° C. for hyperthermally treating said tissue without releasing said second fluorescent dye from said second liposomes.

25. The method of claim 24, wherein said bioactive compound is selected from the group consisting of anti-proliferative agents and anti-tumor agents.

26. The method of claim 24, wherein said bioactive compound is cis-platin.

27. The method of claim 24, wherein said bioactive compound is a photoactivated compound, and wherein said method comprises activating said photoactivated compound to kill or inhibit multiplication of cells in said target site.

28. The method of claim 19, wherein said tissue is heated to a temperature of about 47° C. to about 49° C.

29. The method of claim 19, wherein said second temperature sensitive liposomes leak or rupture at a temperature of about 50° C. to 60° C.

30. The method of claim 1, further comprising heating said target site to a temperature of about 47° C. to about 49° C.

31. The method of claim 1, wherein said liposome releases said dye at a temperature of about 50° C. to about 60° C., and monitoring release of said second dye from said second liposomes and reducing the temperature of said tissue in said target site to 49° C. or less in response to a detection of said second dye released from said second liposomes.

32. The method of claim 1, wherein said target site is in the eye.

33. The method of claim 19, wherein said target site is in the eye.

34. The method of claim 19, wherein said tissue in said target site is heated to a temperature below the temperature where said second dye is released from said second temperature sensitive liposome.

35. The method of claim 19, further comprising monitoring and detecting release of said second fluorescent dye from said second heat sensitive liposome by fluorescing said second fluorescent dye, and reducing the temperature of said tissue in said target site when release of said second fluorescent dye is detected.

* * * * *